United States Patent [19]

Gujarathi et al.

[11] Patent Number: 4,933,484

[45] Date of Patent: Jun. 12, 1990

[54] METHOD FOR REDUCING THE CONCENTRATION OF ACRYLONITRILE IN AN AQUEOUS-ACRYLONITRILE VAPOR STREAM

[75] Inventors: Ramesh N. Gujarathi, Akron; Carole I. Wendt, N. Canton, both of Ohio; Edward K. Kazanjian, Irvine, Calif.; Ann M. Jones, Simpensville, S.C.

[73] Assignee: The Goodyear Tire & Rubber Company, Akron, Ohio

[21] Appl. No.: 303,876

[22] Filed: Jan. 30, 1989

[51] Int. Cl.$^5$ ............................................. C07C 121/32
[52] U.S. Cl. ................................................... 558/463
[58] Field of Search .......................................... 558/463

[56] References Cited

U.S. PATENT DOCUMENTS

| | | | |
|---|---|---|---|
| 3,579,307 | 5/1971 | Wakita et al. | 558/463 X |
| 3,663,631 | 5/1972 | Takeya et al. | 558/463 X |
| 3,663,632 | 5/1972 | Takeya et al. | 558/463 X |
| 4,278,582 | 7/1981 | Miller | 558/463 X |

FOREIGN PATENT DOCUMENTS

| | | | |
|---|---|---|---|
| 42-13456 | 7/1967 | Japan | 558/463 |
| 44-8210 | 4/1969 | Japan | 558/463 |
| 47-43932 | 11/1972 | Japan | 558/463 |
| 210146 | 2/1968 | U.S.S.R. | 558/463 |

Primary Examiner—Joseph P. Brust
Attorney, Agent, or Firm—Bruce J. Hendricks

[57] ABSTRACT

The present invention relates to a process for reducing the concentration of acrylontrile in an aqueous-acrylonitrile vapor stream. The process involves feeding the aqueous-acrylontrile vapor stream to a primary condenser maintained at a temperature and pressure so that a substantial amount of the water is condensed and the acrylonitrile is maintained in the vapor phase. The vapor containing the acrylonitrile from the first condenser is introduced to a secondary condenser maintained at a temperature and pressure so that substantially all the vapor is condensed. The condensate exiting the secondary condenser is introduced to a decanter where the acrylonitrile containing organic phase of the condensate is separated and recovered from the aqueous phase. The aqueous phase is recycled to the primary condenser to significantly reduce the acrylonitrile level in the aqueous phase and enhanced the separation.

8 Claims, 2 Drawing Sheets

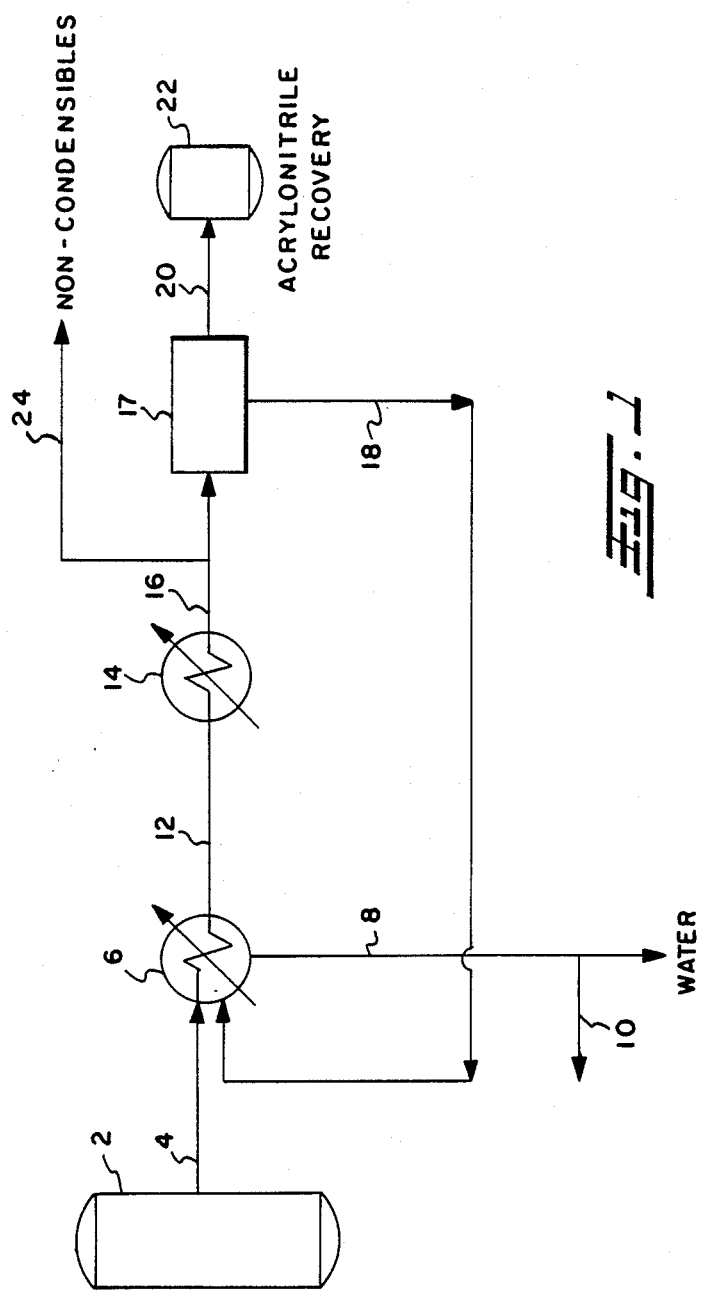

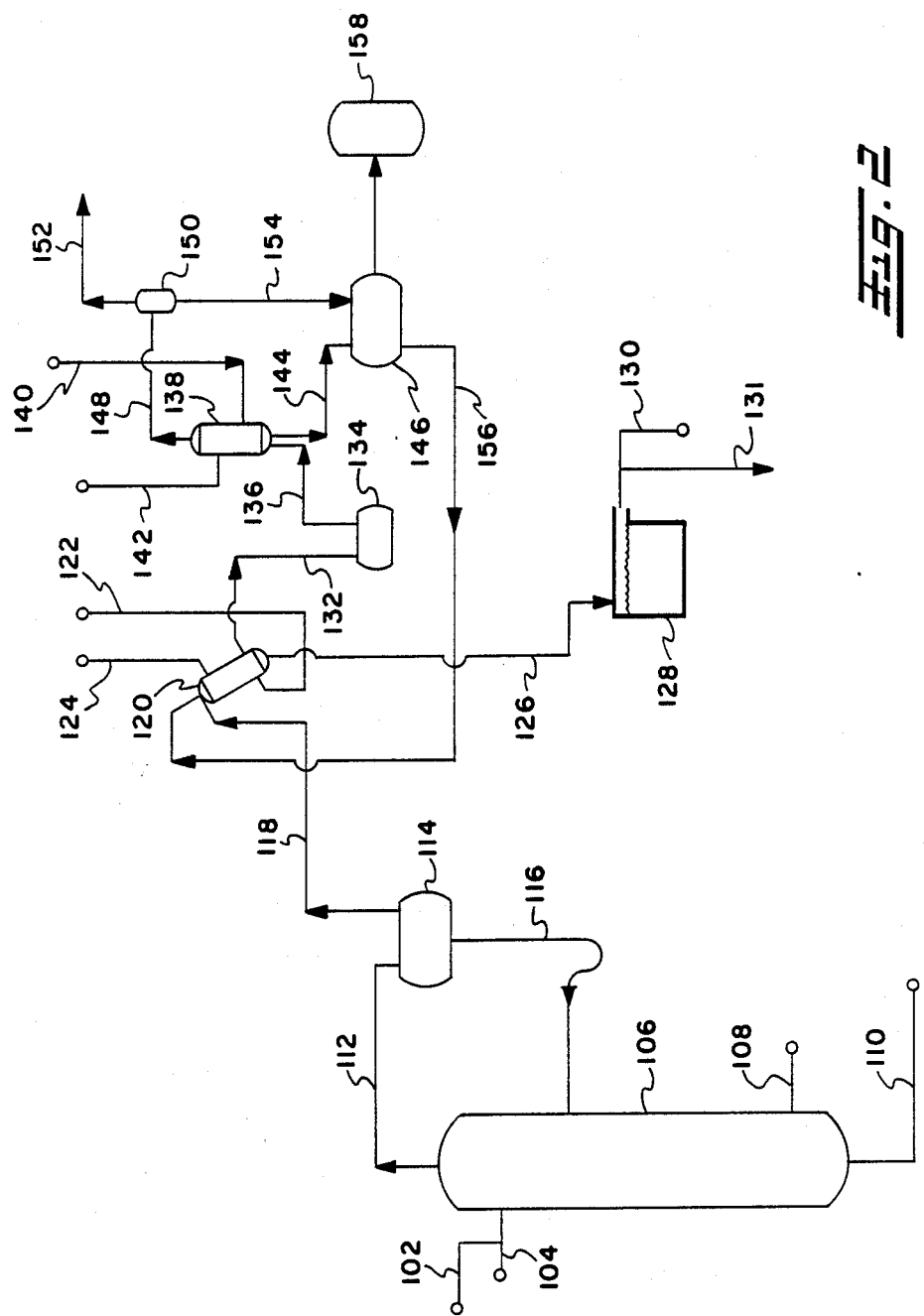

METHOD FOR REDUCING THE CONCENTRATION OF ACRYLONITRILE IN AN AQUEOUS-ACRYLONITRILE VAPOR STREAM

BACKGROUND OF THE INVENTION

Acrylonitrile is a monomer that is widely used in the synthesis of a vast variety of polymers. Acrylonitrile polymers, especially elastomers, are normally synthesized by emulsion polymerization in an aqueous medium. Upon completion of the polymerization, the unpolymerized residual acrylonitrile remains in the aqueous system. Conventional vacuum and steam stripping is used to reduce the residual acrylonitrile in the latex. Since acrylonitrile is believed to be toxic, one may not discharge the aqueous-acrylonitrile medium into the environment. Therefore, it would be desirable to minimize the amount of acrylonitrile in the aqueous phase for the safe disposal in the environment or minimize the acrylonitrile by-product formation to render it more suitable for recycle in a polymerization process.

SUMMARY OF THE INVENTION

The present invention relates to a process for reducing the concentration of free acrylonitrile in an aqueous-organic feed stream comprising:
(a) feeding an aqueous-organic feed vapor stream containing a concentration of from about 1.0 to about 70.0 weight percent acrylonitrile to a primary condenser operated at a temperature and pressure so that about 50 to about 95 weight percent of the water in the vapor stream is condensed and that substantially all the acrylonitrile is maintained in the vapor phase;
(b) feeding the vapor containing acrylonitrile from the primary condenser to a secondary condenser where substantially all of the vapor is condensed to form a condensate; and
(c) separating the acrylonitrile containing organic phase from the aqueous phase in the condensate exiting the secondary condenser.

BRIEF DESCRIPTION OF THE DRAWING

FIG. 1 is a schematic representation of the present invention as applied to the method of reducing the concentration of acrylonitrile in an aqueous-acrylonitrile vapor stream.

FIG. 2 is a schematic representation of a preferred embodiment of the present invention.

DETAILED DESCRIPTION OF THE INVENTION

The acrylonitrile recovery system of the present invention is generally preceded by at least one steam/vacuum stripping column. Various methods and equipment for achieving steam/vacuum stripping of a rubber latex are known to those skilled in the art. It is the vapor stream exiting such stripping columns that serve as the feedstock for the process of the present invention.

The present process can be used to treat an aqueous emulsion containing free acrylonitrile. This process may be useful in connection with the manufacture of acrylonitrile. This process is particularly useful in removing acrylonitrile from aqueous streams resulting from vacuum/steam stripping used to remove residual acrylonitrile from latex. For example, this process is particularly useful as a downstream processing step from the preparation of nitrile rubbers by the copolymerization of butadiene and acrylonitrile. As known to those skilled in the art, the monomer ratio between acrylonitrile and butadiene in nitrile rubbers may be varied over a wide range, however, normally no more than 50 percent of the nitrile rubbers' chain linkages are derived from acrylonitrile. Other comonomers that may be polymerized with acrylonitrile to form polymers in which this process of removing residual acrylonitrile is useful including styrene, isoprene, alkyl acrylates, such as methyl acrylate, ethyl acrylate, butyl acrylate, methyl methacrylate and the like: vinylidene monomers having one or more terminal $CH_2=C<$ groups: vinyl aromatics such as $\alpha$-methylstyrnee, bromostyrene, chlorostyrene, fluorostyrene, vinylphenol, 3-hydroxy-4-methoxystyrene, vinylanisole, $\beta$-nitrostyrene, and the like; $\alpha$-olefins such as ethylene, vinyl halides, such as vinylbromide, chloroethene (vinylchloride), vinylfluoride, vinyliodide, 1,2-dibromoethane, 1,1-dichloroethylene (vinylidene chloride), 1,2-dichloroethylene, and the like; vinyl esters such as vinyl acetate, $\alpha,\beta$-olefinically unsaturated nitriles, such as methacrylonitrile, $\alpha,\beta$-olefinically unsaturated amides such as acrylamide, N-methyl acrylamide, N-t-butyl acrylamide, N-cyclohexyl acrylamide, diacetone acrylamide, methacrylamide, N-ethyl methacrylamide, and the like: $\alpha,\beta$-olefinically unsaturated N-alkylol amides having the general structural formula:

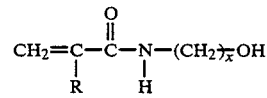

wherein R is a hydrogen atom or an alkyl group containing from 1 to 4 carbon atoms and x is an integer from 1 to 4 inclusive, such as N-methylol acrylamide, N-ethylol acrylamide, N-propylol acrylamide, N-methylol methacrylamide, N-ethylol methacrylamide, and the like; vinyl pyridine; n-octyl methacrylate, dodecyl methacrylate, methyl ethacrylate and ethyl ethacrylate: haloalkyl acrylates such as chloropropyl acrylate; methacrylates, hydroxyethylacrylate; polyfunctional compounds such as ethylene glycol dimethacrylate, diethylene glycol diacrylate, divinyl benzene, alkenyl pentaerythritol, methylene-bis-acrylamide, and the like; $\alpha,\beta$-olefinically unsaturated carboxylic acids containing from 3 to 10 carbon atoms such as methacrylic acid, acrylic acid, crotonic acid, $\beta$-acryloxy propionic acid, sorbic acid, hydrosorbic acid, $\alpha$-chlorosorbic acid, cinnamic acid, $\beta$-styrlacrylic acid, itaconic acid, citraconic acid, maleic acid, fumaric acid, mesaconic acid, aconitic acid, and glutaconic acid.

In the polymerization of acrylonitrile monomer with one or more of the above-mentioned monomers, there can be competing or side reactions which take place. Therefore, the choice of reactants, process conditions, order of addition of the reactants and the like should be selected in order to produce a useful polymer containing acrylonitrile linkages. In general, the resulting copolymer, terpolymer or multimonomer polymer should contain at least about 5 percent by weight of acrylonitrile, If the polymer is a copolymer with acrylonitrile, the acrylonitrile portion may be as high as about 95 percent by weight of the resulting copolymer. The polymers which are preferred are polyacrylonitrile, butadiene-acrylonitrile copolymers, styrene-butadiene-acrylonitrile terpolymers, and carboxylated acrylonitrile-butadiene polymers containing methacrylic, acrylic, itaconic and other like carboxylic monomers.

The present invention is useful with any conventional polymerization techniques. Emulsifiers used in such conventional polymerizations may be charged at the outset of the polymerization or may be added incrementally or by proportioning as the reaction proceeds. Generally, anionic emulsifier systems provide good results, however, any of the general types of anionic, cationic or nonionic emulsifiers may be employed in the polymerization. Normally, such an emulsion polymerization can be run over a very wide temperature range, with good results being obtained when the reaction is run from about 5° C. to about 80° C. for many common polymers. The polymerization of these acrylonitrile containing polymers may be initiated using free radical initiators alone or in combination with redox systems, ultraviolet light, or radiation. To insure a satisfactory polymerization rate, uniformity, and a controllable polymerization, free radical initiators are generally used with good results. Free radical initiators which are commonly used include the various peroxygen compounds such as potassium persulfate, ammonium persulfate, benzoyl peroxide, hydrogen peroxide, di-t-butyl peroxide, dicumyl peroxide, 2,4-dichlorobenzoyl peroxide, decanoyl peroxide, lauroyl peroxide, cumene hydroperoxide, p-menthane hydroperoxide, t-butyl hydroperoxide, acetyl acetone peroxide, methyl ethyl ketone peroxide, succinic acid peroxide, dicetyl peroxydicarbonate, t-butyl peroxyacetate, t-butyl peroxymaleic acid, t-butyl peroxybenzoate, acetyl cyclohexyl sulfonyl peroxide, and the like: the various azo compounds such as 2-t-butylazo-2-cyanopropane, dimethyl azodiisobutyrate, azodiisobutyronitrile, 2-t-butylazo-1-cyanocyclohexane, 1-t-amylazo-1-cyanocyclohexane, and the like; the various alkyl perketals, such as 2,2-bis-(t-butylperoxy)butane, ethyl 3,3-bis(t-butylperoxy)butyrate, 1,1-d-(t-butylperoxy) cyclohexane and the like.

The water soluble and insoluble peroxygen free radical initiators are especially useful in aqueous emulsion polymerization. It may be desirable to add post-polymerization emulsifiers and stabilizers, which will not interfere with this process for removing residual acrylonitrile.

The details and advantages of the invention will be better understood from a consideration of FIG. 1 which is a flow sheet illustrating the sequence of steps for reducing the concentration of free acrylonitrile in an aqueous-acrylonitrile vapor stream. In accordance with the present invention, an aqueous-acrylonitrile vapor stream is received from an upstream source (2). The source (2) may be derived from the manufacture of acrylonitrile or any number of conventional stripping columns known to those skilled in the art. In a preferred embodiment, the upstream source (2) is a steam stripping column containing a number of trays and operating at a temperature ranging from about 100° to about 160° F.and a pressure ranging from about 90° to about 220 mm of Hg when clean. In accordance with the preferred embodiment, the steam stripping column is operated at a temperature ranging from about 120° to about 150° F. with a pressure ranging from about 110 mm to about 150 mm of Hq. As can be appreciated by those skilled in the art, the flow rate of the latex to the source (2) may vary widely but will generally range from about 30 to about 50 gallons per minute with a range of from about 35 to about 40 being preferred.

The aqueous-acrylonitrile vapor stream exiting the source (2) is charged via line (4) to the first condenser (6). The aqueous-acrylonitrile vapor stream may contain a wide range of operating conditions and feed stream acrylonitrile depending on the efficiency of the stripping columns or other means at the source (2). Specifically, the level of acrylonitrile may range from about 1.0 to about 70.0 weight percent with a range of from 2.0 to 25 weight percent being preferred. In addition to water and free acrylonitrile, the aqueous-acrylonitrile vapor stream may contain polymer, 1,3-butadiene, styrene and carboxylic acid monomers. The amount of vapor entering the condenser (6) may vary widely depending on the size of the condensers and may range from about 1000 to about 3000 pounds of vapor per hour. The vapor stream may enter the first condenser (6) at approximately the same temperature as the source (2), however, there may be a slight pressure drop. The internal condition of the first condenser (6) includes a temperature corresponding to about 2° F. below the dew point of the mixture at the operating temperature. The temperature may, therefore, range from about 115° F. to about 150° F., with a range of from about 120° F. to about 125° F. being preferred and a pressure range from about 80 mm to about 160 mm of Hg with a range of from about 110 to about 120 mm of Hg being preferred. Generally speaking, from about 50 to about 95 weight percent of the vapor stream is condensed to a liquid. Preferably, sufficient liquid is condensed to allow a two phase system in the downstream means of separation. The object of the primary condenser (6) is to remove a substantial amount of the water in the aqueous-acrylonitrile vapor stream but yet not condense any organic compounds in the vapor stream.

The condensate from the primary condenser (6) is feed via line (8) to a discharge site (not shown) e.g. sewer or the condensate may be optionally recycled to the upstream polymerization process via line (10).

The vapor stream exiting the primary condenser (6) via line (12) is feed to a secondary condenser (14). The vapor stream may contain from about 40 to about 70 weight percent of an aqueous phase with the remaining weight percent comprising an organic phase, which is predominantly acrylonitrile. The secondary condenser is maintained at a suitable temperature and pressure in order that substantially all the vapor is condensed and, in particular, the acrylonitrile component. Generally speaking, if one maintains the same pressure in the secondary condenser as in the primary condenser, the temperature may range from about 40° F. to about 70° F. If one raises the pressure in the secondary condenser to a range of from about 240 mm to about 340 mm of Hg, the temperature in the secondary condenser ranges from about 85° F. to about 120° F. Preferably, the temperature ranges from about 55° F. to about 60° F. and the pressure ranges from about 100 to about 120 mm of Hg. The condensate from the secondary condenser (14) is feed via line (16) to a decanter (17) where the aqueous phase is separated from the organic phase. The aqueous phase is removed from the decanter by line (18) for recycle to the primary condenser (6) in order to enhance recovery and reduce sewer emissions. The aqueous phase generally contains from about 3 to about 7 weight percent of acrylonitrile. The acrylonitrile containing organic phase is removed and feed via line (20) to an acrylonitrile storage site (22). The organic phase generally contains from about 90 to about 98 weight percent of acrylonitrile. Preferably, the range of acrylonitrile ranges from about 92 to about 96 weight percent. The non-condensibles from the decanter may be removed via line (24) and further processed to any number of recovery sites (not shown).

A more specified embodiment of the present invention can be seen with respect to FIG. 2. Desuperheated steam via line (102) is combined with latex in line (104). The desuperheated steam and latex are then conveyed via line (104) to a steam stripping column (106). An additional source of desuperheated steam is introduced to the steam stripping column (106) via line (108). The stripped latex is discharged from the stripping column (106) via line (110) to a further processing site (not shown). The vaporous stream exiting the stripping column (106) is conveyed via line (112) to a foam trap (114). From the foam trap (114), entrained latex is recycled to the stripping column by line (116). The vapor exiting the foam trap (114) is feed to the primary condenser (12) via line (118). Coolant, i.e., water is supplied to the primary condenser (120) via line (122) and the coolant is removed from the primary condenser (120) via line (124). Condensate from the primary condenser (120) is conveyed via line (126) to a barometric seal tank (128). From the barometric seal tank (128), the condensate is discharged via line (130) to a sewage facility (not shown) or recycled to an upstream polymerization process via line (131). Vapor exiting the primary condenser (120) is conveyed via line (132) to a primary knock out tank (134). From the knock out tank (134), the vapor is conveyed via line (136) to the secondary condenser (138) where substantially all of the remaining vapor is condensed. The coolant, i.e., water, is feed to the secondary condenser (138) via line (140) and taken away from the secondary condenser (138) via line (142). The condensate from the secondary condenser (138) is removed and conveyed by line (144) to a decanter (146). Any non-condensibles not condensed in the secondary condenser (138) are removed by line (148) and feed to a secondary knock out tank (150). Any remaining monomers in vapor form that exit the secondary knock out tank (150) are conveyed via line (152) to a monomer recovery site (not shown). Any liquid from the secondary knock out tank (150) is recycled via line (154) to the decanter (146). Any aqueous phase contained in the decanter (146) is recycled via line (156) to the secondary condenser (138) since the aqueous phase may contain residual amounts of recoverable acrylonitrile. The organic phase containing the desired acrylonitrile is conveyed to a holding tank (158) where the acrylonitrile may be recycled or stored for future use.

In accordance with the process of the present invention, the concentration of free acrylonitrile may be significantly reduced to levels as low as from about 0.2 weight percent to about 1.0 weight percent.

The following examples are provided to illustrate and not limit the scope of the present invention.

EXAMPLE 1

To a recovery system illustrated by FIG. 2 was charged a feed stream comprising 358 lbs./hr. acrylonitrile, 45 lbs./hr. of butadiene and 1976 lbs./hr. of water. The feed stream was 15 percent by weight acrylonitrile. The primary condenser was maintained at a temperature of 122° F. and a pressure of 110 mm of Hg. The secondary condenser was maintained at a temperature of 60° F. and a pressure of 105–108 mm of Hg. Approximately 93% by weight or 333 lbs./hr. of the acrylonitrile were separated and recovered from the vapor feed stream.

EXAMPLE 2

The same recovery system and operating conditions were used as in Example 1 except the vapor feed stream comprised 177.5 lbs./hr. of acrylonitrile, 45 lbs./hr. butadiene and 2157 lbs./hr. of water. The vapor feed stream was about 7.4 percent by weight acrylonitrile. Approximately 86% by weight or 152 lbs./hr. of the acrylonitrile were separated and recovered from the vapor feed stream.

EXAMPLE 3

The same recovery system and operating conditions were used as in Example 1 except the vapor feed stream comprised 77 lbs./hr. of acrylonitrile, 56 lbs./hr. butadiene and 2636 lbs./hr. of water. The vapor feed stream was about 2.8% by weight of acrylonitrile. Approximately 58% by weight or 45 lbs./hr. of acrylonitrile were separated and recovered from the vapor stream.

What is claimed is:

1. A process for reducing the concentration of acrylonitrile in an aqueous- organic feed stream exiting a steam stripping column comprising:
   (a) feeding the aqueous- organic feed stream containing a concentration of from about 1.0 to about 70.0 weight percent acrylonitrile to a primary condenser operated at a temperature and pressure so that from about 50 to about 95 weight percent of the water is condensed and substantially all of the acrylonitrile is maintained in the vapor phase;
   (b) feeding the vapor exiting the primary condenser to a secondary condenser where substantially all said vapor is condensed to form a condensate;
   (c) separating the acrylonitrile containing organic phase from the aqueous phase in said condensate;
   (d) recycling said aqueous phase to said primary condenser.

2. A process for reducing the concentration of acrylonitrile in an aqueous- organic feed stream exiting a steam stripping column comprising:
   (a) feeding an aqueous- organic feed stream containing a concentration of from about 1.0 to about 70.0 weight percent acrylonitrile to a primary condenser operated at a temperature ranging from about 115° F. to about 150° F. and a pressure ranging from about 80 mm of Hg to about 160 mm of Hg wherein from about 50 to about 95 weight percent of the water in said stream is condensed;
   (b) feeding the acrylonitrile containing vapor exiting said primary condenser to a secondary condenser operated at approximately the same pressure as the primary condenser and a temperature from about 40° F. to about 70° F. wherein substantially all the acrylonitrile is condensed to form a condensate;
   (c) feeding the condensate exiting said secondary condenser to a decanter where the acrylonitrile containing organic phase of said condensate exiting said secondary condenser is separated from the aqueous phase;
   (d) recycling said aqueous phase to said primary condenser.

3. A process for reducing the concentration of free acrylonitrile in a latex comprising:
   (a) steam stripping said latex to produce a vapor stream containing acrylonitrile and water;

(b) feeding said vapor stream to a primary condenser wherein from about 50 to about 95 weight percent of the water in said stream is condensed;
(c) feeding said vapor phase to a secondary condenser when substantially all said vapor is condensed to form a condensate: and
(d) separating the acrylonitrile containing organic phase from the aqueous phase in said condensate;
(e) recycling said aqueous phase to said primary condenser.

4. The process of claim 1 wherein the condensate exiting said secondary condenser is passed to a decanter where the organic phase of said condensate is separated from the aqueous phase.

5. The process of claim 1 wherein the concentration of acrylonitrile in said aqueous- organic stream ranges from about 2.0 to about 25 weight percent.

6. The process of claim 2 wherein said recycled aqueous phase of said condensate from said secondary condenser contains from about 3 to about 7 weight percent acrylonitrile.

7. The process of claim 3 wherein said organic phase of said condensate contains from about 90 to about 98 weight percent acrylonitrile.

8. The process of claim 3 wherein said recycled aqueous phase contains from about 3 to about 7 weight percent acrylonitrile.

* * * * *